United States Patent
Hack

(10) Patent No.: US 8,641,731 B2
(45) Date of Patent: Feb. 4, 2014

(54) EMERGENCY SNAKE BITE TREATMENT DEVICES, MEDICAL KITS AND RELATED METHODS

(75) Inventor: Jason B. Hack, East Greenwich, RI (US)

(73) Assignee: East Carolina University, Greenville, NC (US)

( * ) Notice: Subject to any disclaimer, the term of this patent is extended or adjusted under 35 U.S.C. 154(b) by 705 days.

(21) Appl. No.: 12/347,012

(22) Filed: Dec. 31, 2008

(65) Prior Publication Data

US 2009/0171384 A1 Jul. 2, 2009

Related U.S. Application Data

(60) Provisional application No. 61/018,553, filed on Jan. 2, 2008.

(51) Int. Cl.
*A61B 17/00* (2006.01)

(52) U.S. Cl.
USPC .......................................................... 606/203

(58) Field of Classification Search
USPC .................. 606/201–203; 604/115, 314–316; 602/53, 63, 75–77; 24/300, 301; 63/3.1, 3.2
See application file for complete search history.

(56) References Cited

U.S. PATENT DOCUMENTS

| | | | |
|---|---|---|---|
| 1,221,103 A | | 4/1917 | Sorensen |
| 2,185,571 A | * | 1/1940 | Robinson ...................... 606/203 |
| 2,936,759 A | * | 5/1960 | Yuhas ............................ 606/203 |
| 3,620,209 A | * | 11/1971 | Kravitz ........................... 601/79 |
| 4,393,867 A | | 7/1983 | Baron |
| 5,235,990 A | | 8/1993 | Dempsey |
| 5,722,260 A | * | 3/1998 | Mangano ........................ 63/3.1 |
| 6,631,282 B2 | * | 10/2003 | Rule et al. ..................... 600/344 |
| 2009/0126163 A1 | * | 5/2009 | Groner ............................ 24/302 |

OTHER PUBLICATIONS

McCullough, Jay (Ed.). (1997)"The Ultimate Guide to U.S. Army Survival Skills, Tactics, and Techniques". New York: Skyhorse Publishing. pp. 135-140.*
Stewart, Carmel. "Snake Bite in Australia: first aid and envenomation management". (2003) vol. 11, pp. 106-111.*
Sawyer Extractor Snake Bite Kit, product listing, http://www.rei.com/product/407144, (1 Sheet) Date unknown but for the purposes of Examination before Jan. 2, 2008.
International Search Report and Written Opinion for corresponding PCT application No. PCT/US2008/014139, Date of mailing May 29, 2009.
Swift First Aid Snake Bite Kit (Wisemen Trading and Supply Company), http://www.wisementrading.com/firstaid/snake_bite.htm, Oct. 10, 2002.

(Continued)

*Primary Examiner* — Katherine Dowe
(74) *Attorney, Agent, or Firm* — Myers Bigel Sibley & Sajovec, P.A.

(57) ABSTRACT

First aid or emergency snake bite treatment devices include a belt or other securing member attached to a compression (bite isolation) member, the compression member having an outwardly projecting wall that is configured to surround the snake bite and compress the skin about the snake bite a distance inward to thereby isolate the venom from the bite to impede the venom from entering a victim's lymphatic system.

22 Claims, 10 Drawing Sheets

(56) References Cited

OTHER PUBLICATIONS

Unit First Aid Kits—Snake Bite Kit (First-Aid Supplies Online Company), http://www.firstaidsuppliesonline.com/nav.pl?cat=NavUnit&prod=3523SB, Aug. 18, 2007.

First Aid Treatment of Snake Bite (University of Canberra, Australia), http://feral.org.au/staff/georges/snaakebite.pdf, Aug. 27, 2007.

Snake Bite First Aid (NC State University), http://www.ces.ncsu.edu/gaston/Pests/reptiles/snakebitetx.htm, Aug. 16, 2004.

* cited by examiner

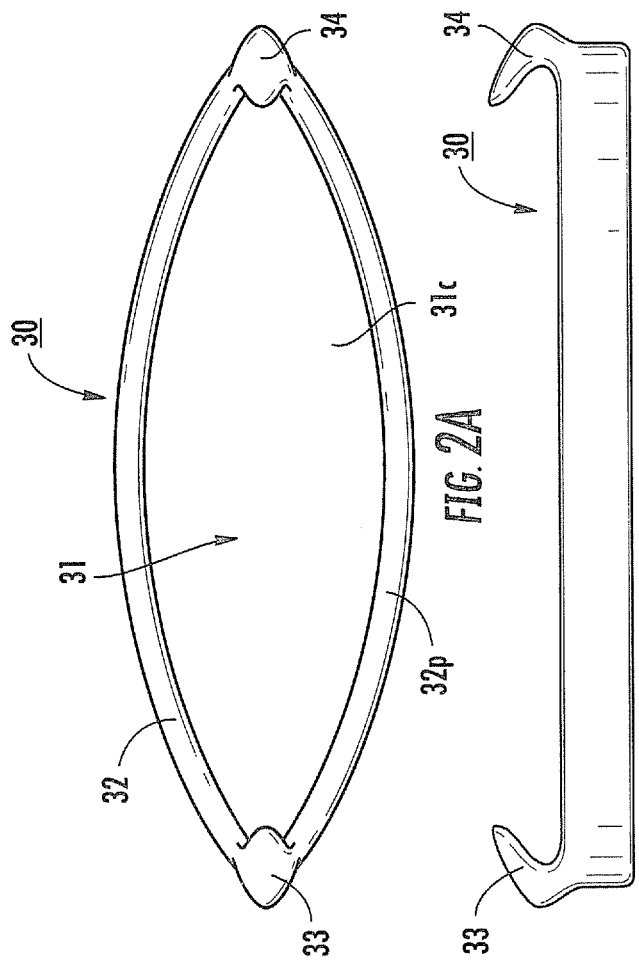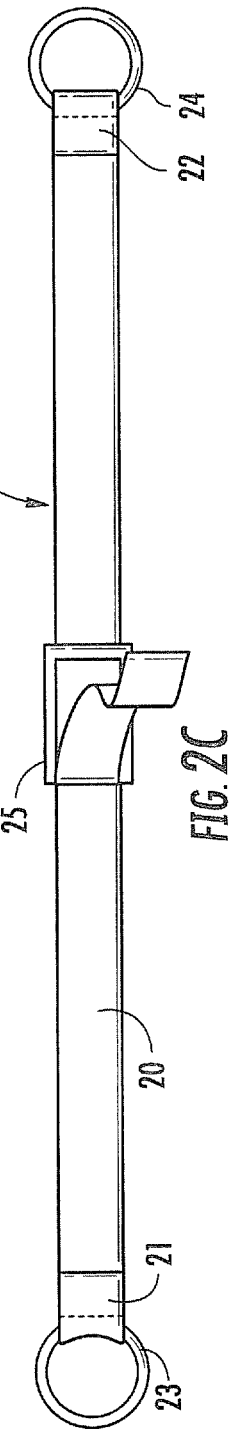

EMERGENCY SNAKE BITE TREATMENT DEVICES, MEDICAL KITS AND RELATED METHODS

RELATED APPLICATION

This application claims the benefit of priority to U.S. Provisional Application Ser. No. 61/018,553, filed Jan. 2, 2008, the contents of which are hereby incorporated by reference as if recited in full herein.

FIELD OF THE INVENTION

This invention relates to first aid venomous snake bite treatment devices.

BACKGROUND OF THE INVENTION

The conventional standard of care for snake bites to distal limbs includes limb immobilization, application of pressure bandages, and immediate medical care (where available). There is no known publication for research on treatments of snake bites to the torso, although suction-type devices are available. Unfortunately, the suction-type devices may not be able to retain sufficient suction around the wound while the victim is transported to a medical facility.

SUMMARY OF EMBODIMENTS

Embodiments of the invention are directed to easy-to-use, light-weight, portable devices that can impede lymphatic flow of the venom from the site of the bite to the systemic circulation to delay onset of toxicity while a patent is delivered to definitive care (e.g., administration of an anti-venom).

Embodiments of the invention provide a belt attached to a compression (bite isolation) member, the compression member having an outwardly projecting wall that is configured to surround the snake bite and compress the skin about the snake bite a distance inward to thereby isolate the venom from the bite to impede the venom from entering a victim's lymphatic system.

The compression member can have an open center that, in position, resides over the snake bite, with the wall configured to extend substantially orthogonally a distance into a victim's body to force the skin to compress thereunder a suitable distance.

Some embodiments are directed to snake bite treatment devices that include a belt or other securing member attached to a compression (bite isolation) member, the compression member having an outwardly projecting wall that is configured to surround the snake bite and compress the skin about the snake bite a distance inward to thereby isolate the venom from the bite to impede the venom from entering a victim's lymphatic system.

Still other embodiments are directed to first aid snake-bite treatment devices that include: (a) a localized compression member having a cavity surrounded by a wall, wherein, in position, the compression member resides on a skin surface of a victim such that the cavity resides over tissue proximate a snake bite and the wall surrounds and compresses localized tissue inward a distance away from and surrounding the snake bite; and (b) a belt having opposing end portions, wherein each end portion is configured to fixedly or releasably attach to laterally opposing end portions of the compression member.

Some embodiments are directed to (portable) snake bite treatment kits that include: (a) at least one belt or other securing member sized and configured to reside about a torso of a person: and (b) a compression member configured to attach to the at least one belt.

Still other embodiments are directed to methods of performing first aid treatment of a venomous snake bite. The methods include: (a) placing a localized compression member over a snake bite region on a surface of skin of a victim; (b) placing a belt around the victim; (c) tightening the belt and securing the compression member to the victim; and (d) compressing the skin of the victim surrounding the snake bite so that the compressed skin is forced inward a distance relative to the skin proximate the snake bite, thereby impeding snake bite venom from migration into a victim's circulatory system.

Other embodiments are directed to methods of performing first aid treatment of a venomous snake bite that include: (a) placing a localized compression member over a snake bite region on a surface of skin of a victim; (b) securing the compression member to the victim; and (c) compressing the skin of the victim surrounding the snake bite so that the compressed skin is forced inward a distance relative to the skin proximate the snake bite thereby impeding snake bite venom from migration into a victim's circulatory system.

Embodiments of the invention may be particularly suitable for torso or proximal extremity bites (but may also be used for treating bites in other areas as well).

Features described with respect to one embodiment can be used with respect to another embodiment.

The foregoing and other objects and aspects of the present invention are explained in detail in the specification set forth below.

BRIEF DESCRIPTION OF THE DRAWINGS

FIG. 2A is a top schematic view of a localized compression member according to embodiments of the present invention.

FIG. 2B is a front view of the device shown in FIG. 1.

FIG. 2C is a top view of a belt suitable for engaging the device shown in FIGS. 2A and 2B according to embodiments of the present invention.

DESCRIPTION OF EMBODIMENTS OF THE INVENTION

Figure 1:
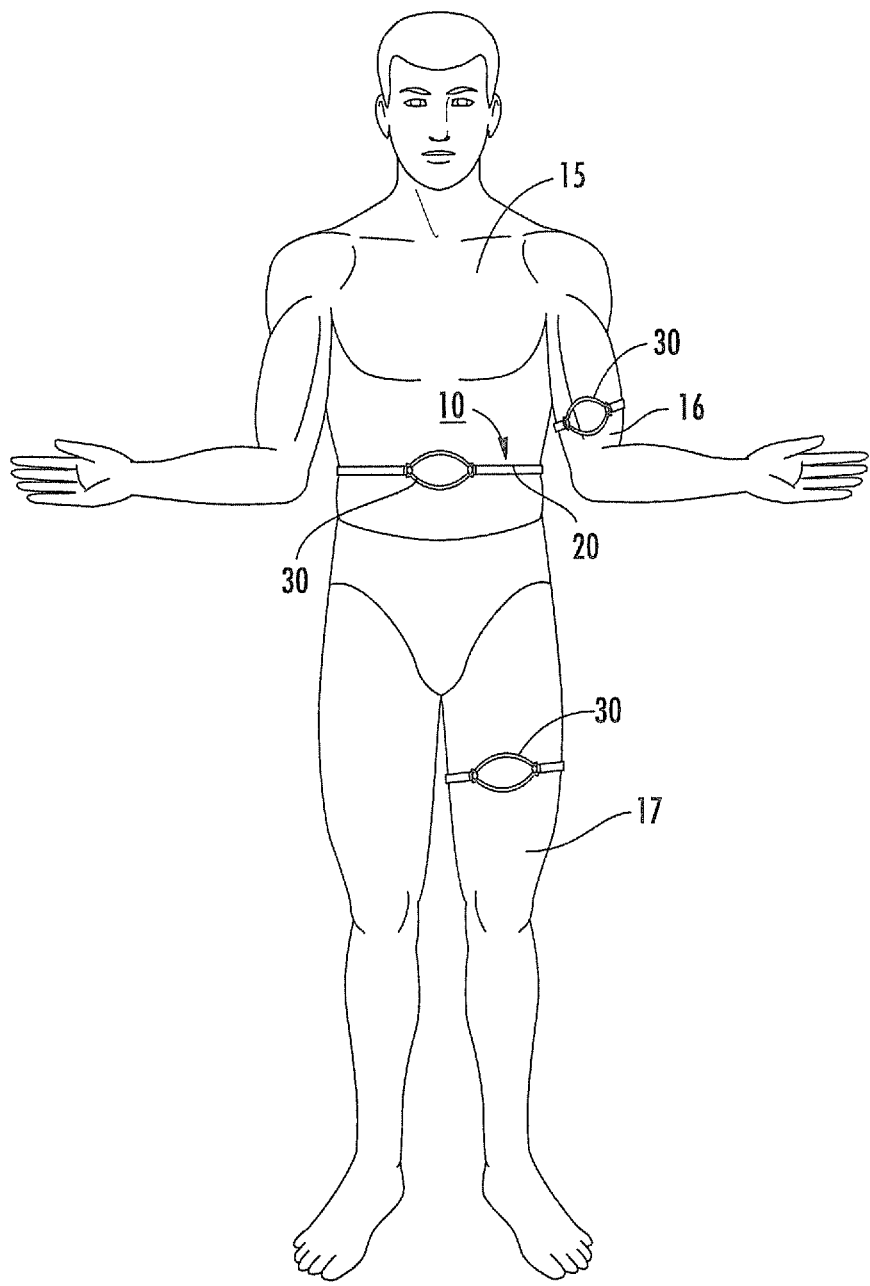
FIG. 1 is a schematic illustration of a localized compression snake bite treatment device suitable for treating proximal extremity and torso snake bite locations according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected". "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

The term "elastomer" and derivatives thereof means that the device comprises a polymer, a copolymer and derivatives and/or combinations thereof.

FIG. 1 illustrates that the snake-bite treatment device 10 can include a securing member 20, such as a band or belt 20 and a compression member 30 that provides localized compression about a snake bite and can be configured for use on the torso 15 as well as a limb, e.g., a proximal extremity such as proximal portion of an arm 16 or leg 17. However, the device 10 may also be used to treat other bites and in other areas.

The belt 20 can comprise cloth, fabric, leather or other suitable, typically elastic, material and/or combinations thereof. The belt 20 can be configured to inhibit slippage even when exposed to sweat, rain or other moisture. The belt 20 can be configured to provide constant tension without loosening over a period of at least two hours, typically at least about 8 hours. The belt 20 can also or alternatively be periodically inspected by a user and tightened by a user as appropriate to maintain the desired compression. The belt 20 can be substantially planar or may be tubular (e.g., a rope-like) configuration or other suitable configuration that has a length sufficient to encircle or extend about the torso and/or limb of a subject. The belt may be provided in S, M, L and XL sizes to fit different anatomical sizes of people or may be provided in a universal size. The belt 20 can be attached to clasp or buckle 25 that allows for almost any desired adjustable length. The compression member 30 can be configured to accept the different belt sizes (e.g., the compression member 30 can be a universal compression member made for use with S, M, L and XL belt sizes.). In other embodiments, the compression member 30 and the belt 20 may be provided in different sizes.

FIGS. 2A and 2B illustrate one embodiment of the compression member 30. As shown, the compression member 30 has a center though-aperture 31 (or open cavity) and a wall 32 with a perimeter 32p that surrounds the aperture 31 defining a cavity 31c. The cavity 31c can be an open cavity, a closed cavity or a partially visually occluded cavity. The member 30 can be an elastomeric, ceramic, or metallic member (or combinations of same) that may be molded, stamped, machined or otherwise formed into the desired configuration. The member 30 can be a unitary monolithic member or may comprise a plurality of integrated components of the same or different materials. The member 30 can be configured to be light weight for ease of portability (e.g., less than about 1 lb and typically about 6 ounces or less), with the actual weight being dependent upon the materials used to form the belt, clasp and compression member.

Figure 4C:
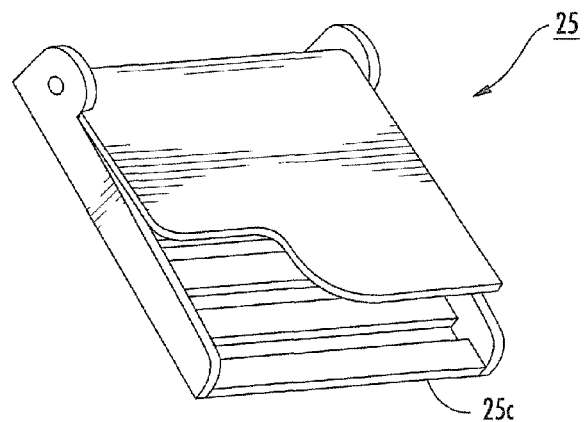
FIG. 4C is a top perspective view of an exemplary belt clasp for use with a belt or strap according to some embodiments of the present invention.

FIG. 2C illustrates that the belt 20 can include opposing free ends 21, 22, each with a compression member connector 23, 24 respectively, that can releasably engage belt connectors 33, 34 of the compression member (FIGS. 2A and 2B). As shown in FIG. 2C, the belt 20 can include a belt tensioner 25 (e.g., clasp) that a user can easily and quickly use to slide or pull to adjust the length of the belt 20 and maintain the desired tension. FIG. 4C illustrates one example of a suitable tensioner 25, shown as a clasp 25c, that allows for adjustability to almost any desired length for use on a number of anatomical positions and different shaped individuals. In some embodiments, the belt 20 can be configured for one-hand adjustment by the victim without requiring the use of another person. However, the invention is not limited thereto as other belt attachment and length adjustment configurations can be employed.

Figure 8:
FIGS. 8-10 are digital photographs of a prototype of a snake bite treatment device attached to torsos of a pig.

The belt 20 is typically adjustable from a short length to fit around the (proximal) limb to a longer length to fit around the torso. In the embodiment shown in FIG. 2C, the connectors 23, 24 have a closed perimeter geometric shape. The connectors 23, 24 may be in an open or closed shape and may have a "D" shape to inhibit rotation or turning during use as is shown in FIG. 8. Other anti-rotation or anti-slip configurations may also be used. For example, an elastomeric increased friction gripping material can be applied to the connector 23, 24 and/or the belt 20 can be configured with a narrow holding channel or otherwise attached to the connectors 23, 24 to inhibit rotation of the connectors (not shown).

Figure 3A:
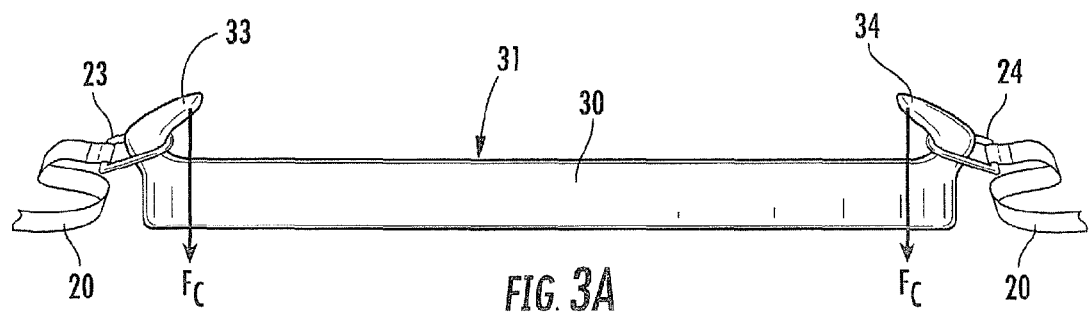
FIG. 3A is a side schematic view of a compression member attached to a tensioning belt in a manner that exerts downward compression according to embodiments of the present invention.

FIG. 3A schematically illustrates that the compression member 30 can be configured so that tensioning of the belt 20 applies a compression force (Fe) that is substantially orthogonal to the surface of the victim so that the member 30 can compress downwardly a sufficient distance to isolate the snake bite tissue and impede the flow of venom into the circulatory system. The belt 20 attaches to an upper portion of the compression member 30. In the embodiment shown, the connectors 33, 34 have a profile when viewed from the side that extends upwardly and inwardly toward each other across the cavity 31c. The outer bounds of the member 30 can have a long dimension of between about 1-6 inches, typically between about 2-5 inches, and a width and/or length in the short dimension of between about 1-4 inches, typically between about 1-3 inches. In some embodiments, the cavity 31c can have similar dimensions. The wall 32 can have a height that is between about 0.25 inches to about 2 inches. The height of the wall 32 may be substantially constant about the entire perimeter or may vary.

Figure 3B:
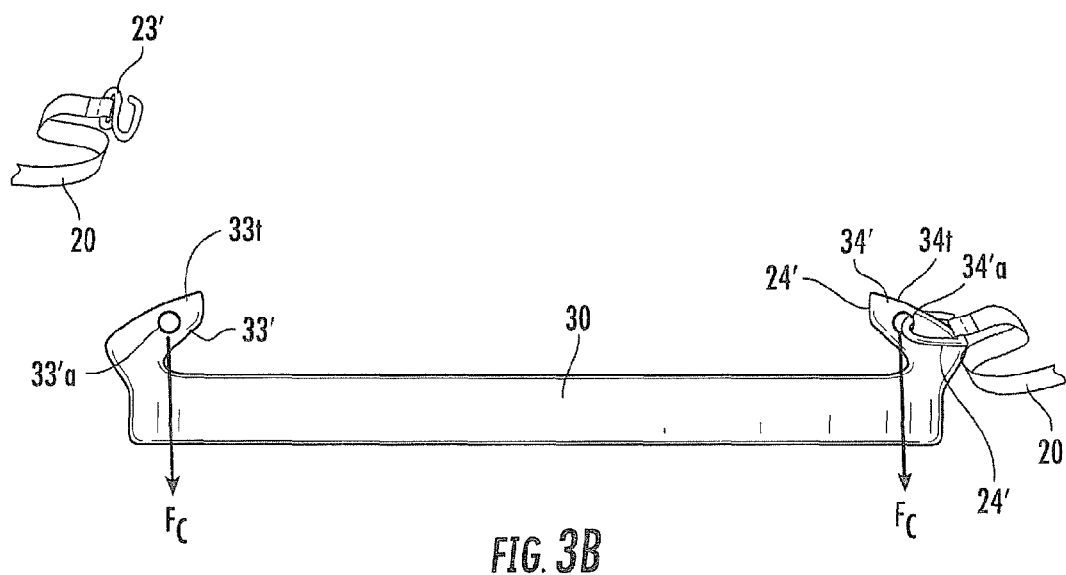
FIG. 3B is a side schematic view of another embodiment of the compression member and belt according to other embodiments of the present invention.

FIG. 3B illustrates alternate configurations of the belt connectors 23', 24' and compression member connectors 33', 34'. As shown, the belt connectors 2', 24' may be fixedly or releasably attached to the compression member connectors 33', 34', which can comprise an aperture in an upwardly extending tab 33t, 34t, with the aperture 33'a, 34'a typically residing a distance inside the outer bounds of the wall 32 of the compression member 30. In some embodiments, one end of the belt 20 may be fixedly attached and the other end of the belt releasably attached to the member 30.

Figure 4A:
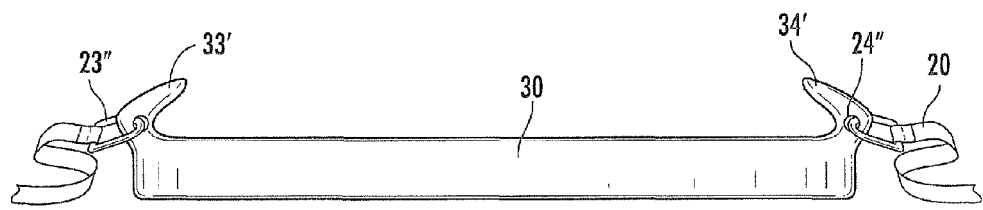
FIGS. 4A and 4B are side schematic views of other configurations of the compression member and/or belt attachment features according to embodiments of the present invention.

FIG. 4A illustrates yet another alternative belt connector 23', 24', this connector configuration being affixed (non-releasable) to the compression member 30 and provided in this configuration in a kit for use in that configuration.

Figure 4B:
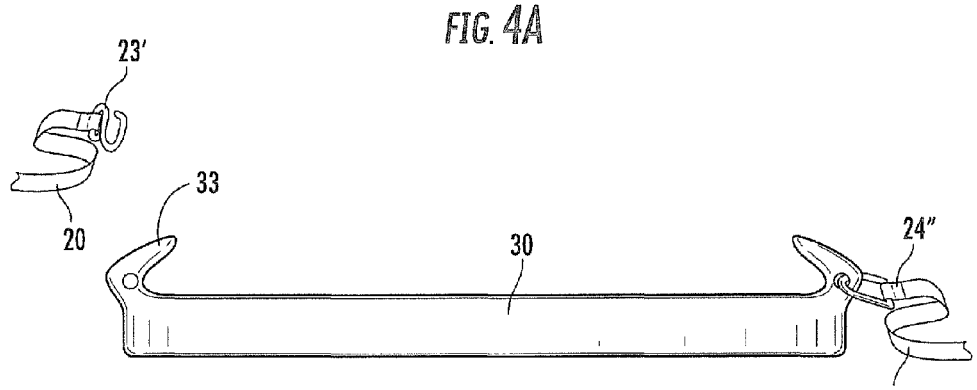

FIG. 4B illustrates that each end of the compression member may have different attachment configurations, and that one end of the compression member 30 can be releasably attached to the belt 20 while the other can be fixedly attached (e.g., integrally attached). However, it may be desirable to configure the attachment and belt connection interface so that a substantially common compression force is exerted by the wall about the entire perimeter of the cavity 31c surrounding the snake bite.

Figure 5A:
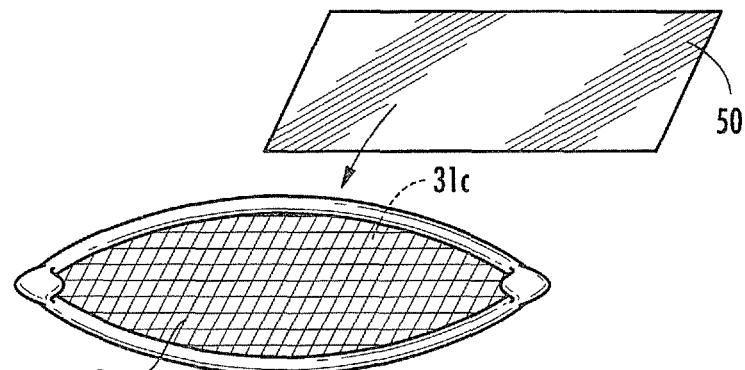
FIG. 5A is a top exploded view of one embodiment of the compression member according to embodiments of the present invention.

FIG. 5A illustrates that the top of the compression member can comprise a covering 50, such as a visually transmissive film or mesh that can provide some protection from the environment while allowing a user to be able view the snake bite location therethrough. The covering 50 can be pre-attached or attached by a user and included as a separate component in a kit. In other embodiments, the member 30 can include a solid upper surface over the cavity 31c forming the compression chamber around the wound/bite mark (not shown).

Figure 5B:
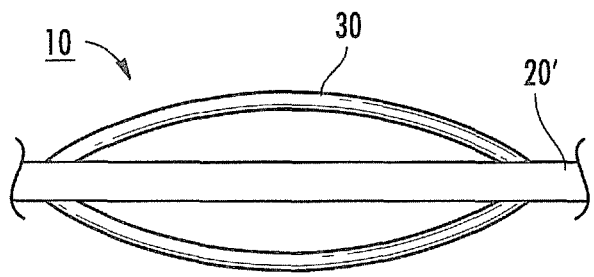
FIG. 5B is a top view of a different securing member configuration according to embodiments of the present invention.

FIG. 5B illustrates an alternative configuration of a securing member 20'. In this embodiment, a strap 20' can extend across the compression member 30 to hold the member in position with sufficient compression force. The strap 20' can include a relatively strong adhesive with sufficient length to extend beyond the perimeter of the member 30 and securely locks to the skin of a user, typically extending at least four inches from each side of the member 30, and can extend substantially around the entire limb or torso. Although not shown, the strap 20' could be two straps that attach to opposing edges of the member rather than a single strap. The strap 20' could be provided in a treatment kit 100 (FIG. 7) in a roll that allows a user to determine the desired length (and a user can wrap the strap over the member 30 a plurality of times and/or around the limb or torso one or more times). In addition, the member 30 can include two strap or tape channels (open or closed) that can reside on a top surface of the member 30 for ease of access/use that can help hold the strap or tape symmetrically across the member or symmetrically extending from a substantially opposing location of the member for better control of compression pressure/force (not shown).

Figure 6A:
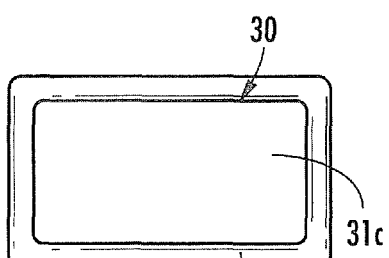
FIGS. 6A-6C are schematic top views of other configurations of the compression member according to embodiments of the present invention.
Figure 6B:
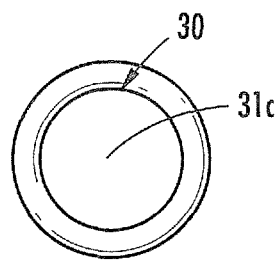
Figure 6C:
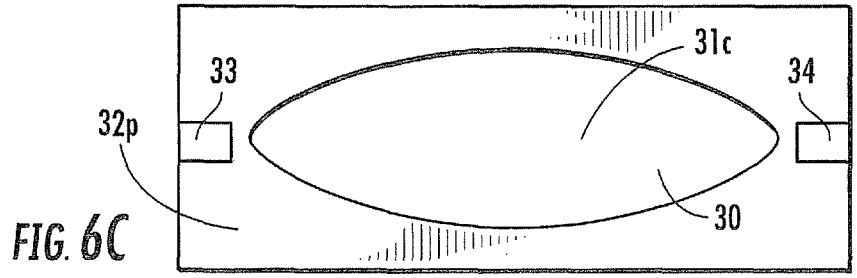

FIGS. 6A and 6B illustrate that the compression member 30 can have a different geometric shape from that shown with respect to the substantially oval or elongated circle shape shown above. FIG. 6A illustrates the perimeter 32p has a substantially rectangular shape while FIG. 6B illustrates a perimeter 32p with a substantially circular shape. The wall perimeter 32p and the cavity 31c shape may be different as shown in FIG. 6C.

Figure 7:
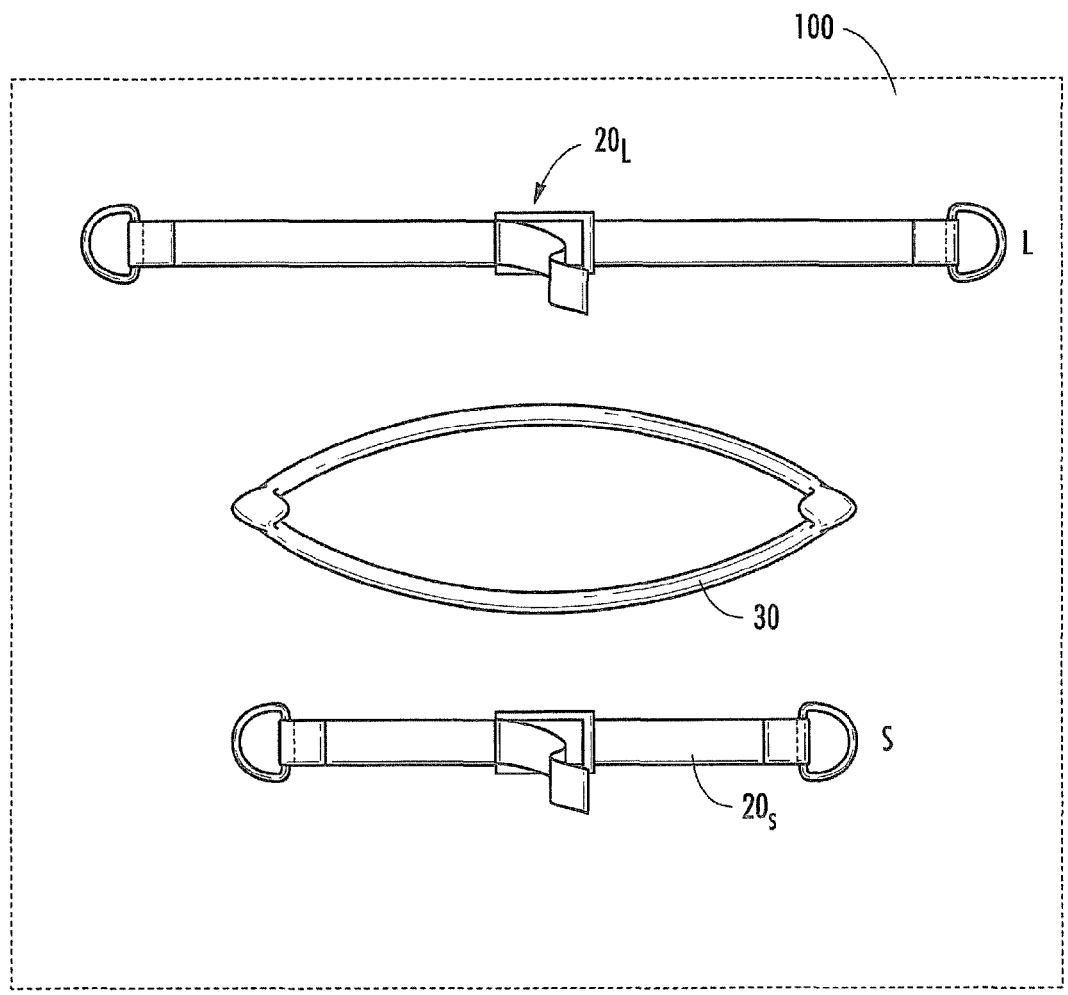
FIG. 7 is a schematic illustration of an emergency/first aid snake bite treatment kit according to embodiments of the present invention.

FIG. 7 illustrates a first aid kit 100 with the device 10. In some embodiments, the kit 100 can include a plurality of different length belts 20, shown as large and small belts 20L, 20S, with the compression member 30. In most uses, there will be no requirement to prepare the bite area by shaving as the device 30 is configured to be able to provide sufficient localized compression without such a preparatory action. However, the kit 100 may be provided with alcohol and shaving components. In some embodiments, the kit 100 can also include a suction member that cooperates with the compression member 30 and belt 20 (not shown).

The present invention is explained in greater detail in the following non-limiting Example.

EXAMPLE

Figure 9:
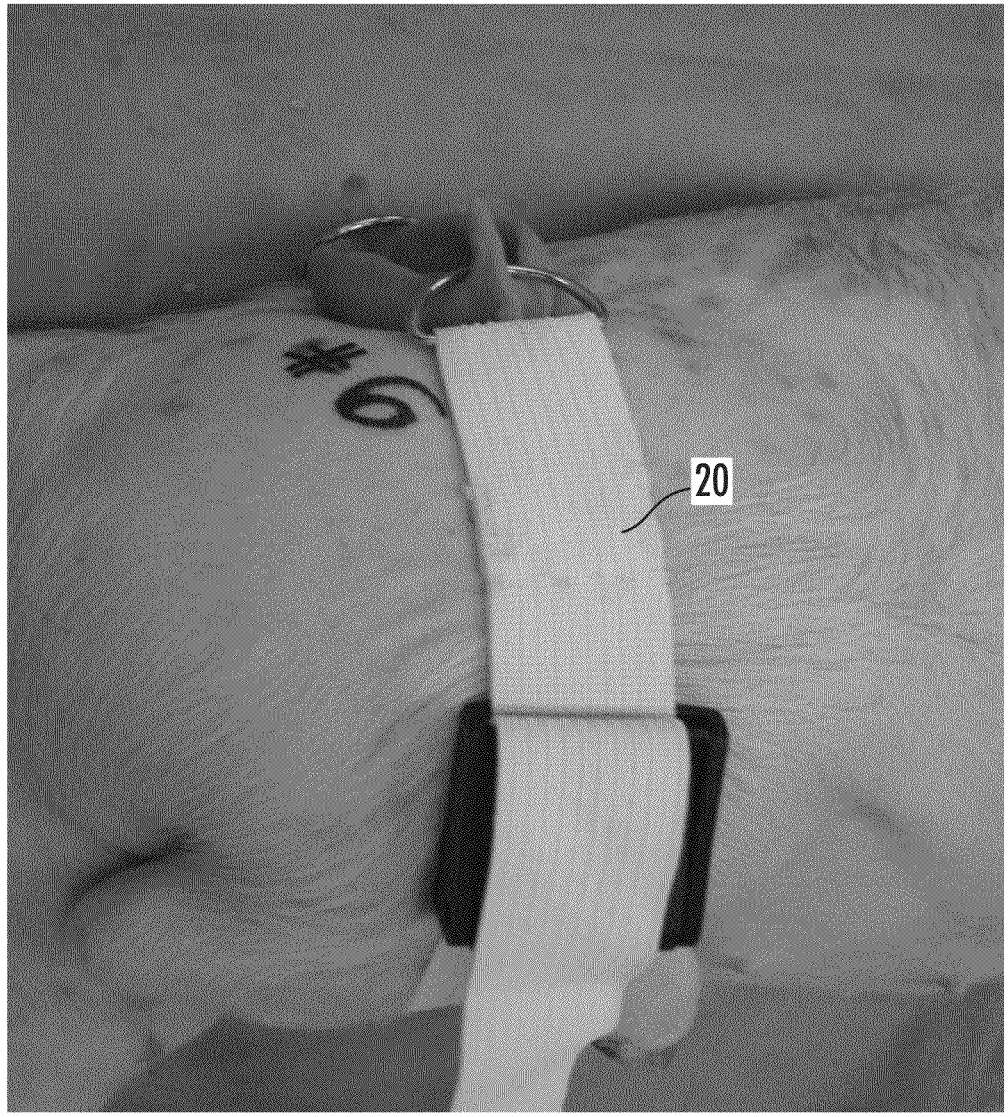
Figure 10:
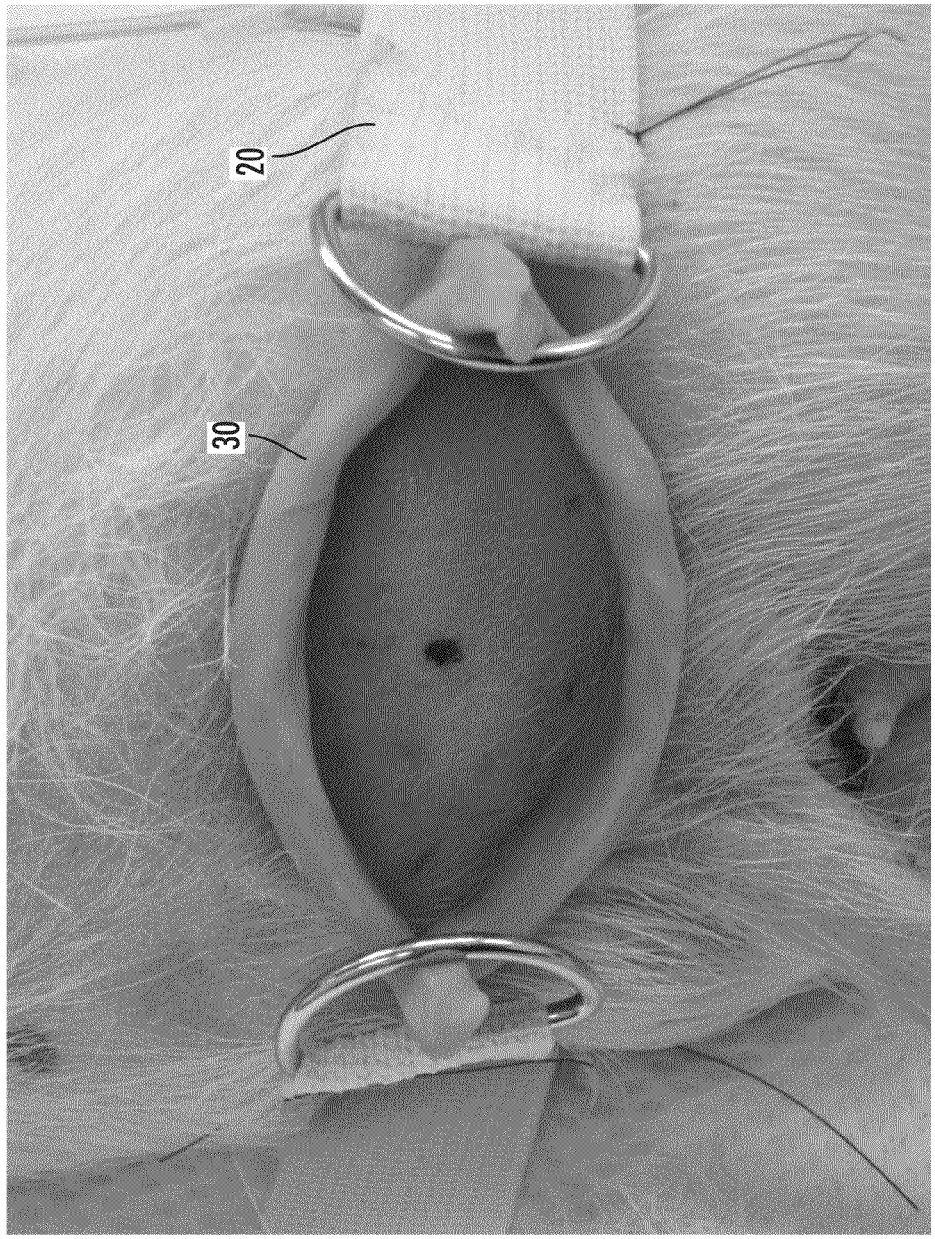

Pigs were injected in the torso with coral snake venom, a potent neurotoxin. Most typical snake bites produce or deliver between about 3-6 mg of venom. The pigs were injected into the torso with 10 mg of snake venom (a fatal dose amount). A prototype of the device as shown in FIGS. 8-10, was used on some of the pigs injected with the snake venom and not used on others (controls). The experiment was performed to assess if the device prolonged the time until the animal stopped breathing.

Figure 11:
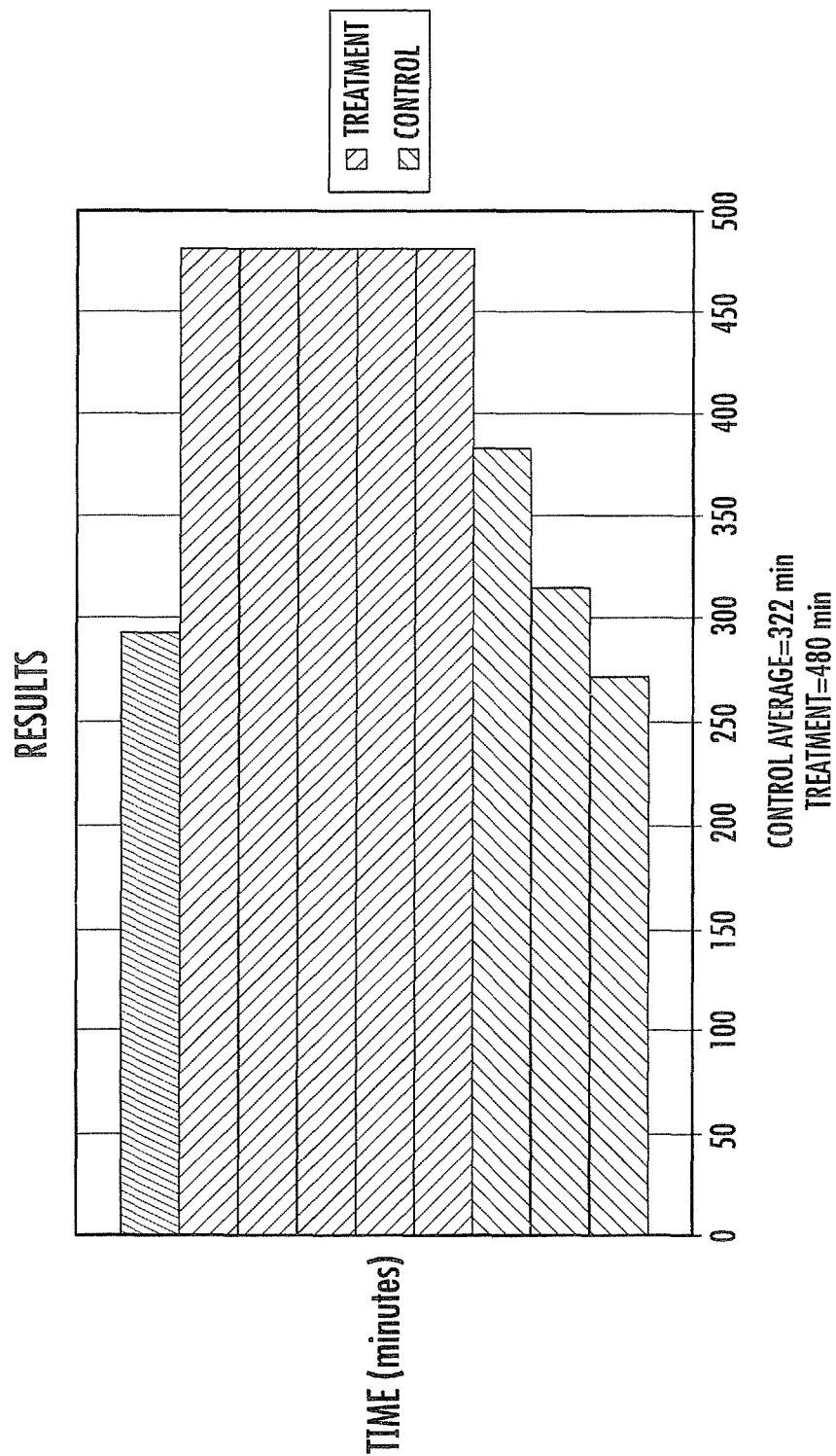
FIG. 11 is a graph of the experimental results of time in minutes to cessation of breathing after administration of a fatal dose of snake venom illustrating the difference or additional time to death for those pigs having the device shown in FIGS. 8-10 versus those with no treatment.

The results shown at FIG. 11 illustrated the additional (prolonged) time provided when the device was used relative to when the device was not used. The control average was 322 minutes while the average for those using the treatment device was 480 minutes (158 minutes longer).

The device 10 may be particularly suitable for wilderness adventurers, such as mountain climbers, hikers, canoeists, kayakers and the like, as well as military field operation personnel, EMS personnel and ambulances, facilities in outlying areas, such as foresters, national park systems and the like, as well as school facilities, urgent care facilities and the like.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A snake bite treatment device, comprising:
a belt;
a compression member configured to cooperate with the belt, the compression member having a monolithic primary body with upwardly projecting connectors on outer edge portions thereof that extend a distance above the primary body and attach to ends of the belt, wherein the primary body has an open center surrounded by a wall that extends downwardly in a direction opposite the connector, and wherein the compression member is configured to surround a snake bite and cooperate with the belt to compress skin in a closed perimeter extending about the snake bite a distance inward sufficient to deform the skin inward relative to skin in a center space of the compression member over the snake bite to isolate venom from the bite to thereby impede the venom from entering a victim's lymphatic system.

2. The device of claim 1, wherein the compression member primary body is a substantially oval frame-like body with a large open center with a long dimension of between about 2-5 inches and a largest width dimension of between about 1-3 inches, and wherein, in position, the large open center resides over the snake bite, and wherein the wall is configured to extend substantially orthogonally a distance and a direction that is into a victim's body to force the skin thereunder to compress a suitable distance.

3. The device of claim 1, wherein the compression member is devoid of suction means and is configured to allow the snake bite to be exposed to atmospheric conditions.

4. The device of claim 1, wherein the compression member has sufficient rigidity to apply a compression force that forces the skin about the bite inward and sufficient flexibility to conform to a curved anatomical body portion of a snake bite victim.

5. The device of claim 1, wherein the belt and compression member are sized and configured for applying localized compression to a snake bite on a victim's torso.

6. The device of claim 1, wherein the compression member has a long dimension of between about 2-5 inches and a width or short dimension of between about 1-3 inches, and wherein securing member is a belt that has a width that is substantially the same as a largest width dimension of the compression body.

7. The device of claim 1, wherein the compression member connectors comprise fingers that rise up and turn in to face each other across the open center, wherein the belt is releasably attachable to one or both of the fingers, and wherein the belt extends outwardly from a respective side of the compression member substantially in line with one or both fingers.

8. A snake bite treatment device, comprising:
a compression member with a cooperating belt, the compression member having a wall that extends downwardly in a direction opposite the belt and has a closed perimeter that surrounds a center space, wherein the wall is configured to surround a snake bite and compress skin in a closed perimeter extending about the snake bite a distance inward sufficient to deform the skin inward relative to skin in the center space of the compression member over the snake bite to isolate venom from the bite to thereby impede the venom from entering a victim's lymphatic system,
wherein the compression member comprises a primary body that defines the wall, the wall extending between upper and lower surfaces of the compression member primary body, wherein the compression member primary body includes first and second spaced apart belt connection members that project outwardly to extend a distance above the upper surface of the primary body and reside on respective outer edge portions of the primary body, with each belt connection member residing on an opposing lateral end of the compression member body, wherein, in position, end portions of the belt attach to the belt connection members of the compression member to define a compression force that is substantially orthogonal to a surface of the skin to thereby compress the skin inward in the closed perimeter.

9. The device of claim 8, wherein the belt connection members each have a finger with an upper end, the finger extending a distance above the upper surface of the primary body of the compression member and having a profile when viewed from the side that angles upwardly and inwardly so that each finger upper end tapers toward each other from an outer edge of the compression member primary body, wherein the belt connection members are configured to releasably engage the belt and hold the belt so that the belt extends in a direction away from the center space, in line with the finger.

10. A snake bite treatment device, comprising:
a compression member with a cooperating belt, the compression member having an outwardly projecting wall that is configured to surround a snake bite and compress skin in a closed perimeter extending about the snake bite a distance inward sufficient to deform the skin inward relative to skin in a center space of the compression member over the snake bite to isolate venom from the bite to thereby impede the venom from entering a victim's lymphatic system,
wherein the compression member comprises a primary body that defines the wall, the wall extending between upper and lower surfaces of the compression member primary body, wherein the compression member primary body includes first and second spaced apart belt connection members that extend a distance above the upper surface of the primary body and reside on respective outer edge portions of the primary body, with each belt connection member residing on an opposing lateral end of the compression member body, wherein, in position, the belt and compression member define a compression force that is substantially orthogonal to a surface of the skin to thereby compress the skin inward in the closed perimeter,
wherein the belt has an adjustable length and comprises first and second opposing end portions with a respective D-shaped rigid connector thereon, and wherein the first and second end portion connectors each releasably engage one of the belt connection members of the compression member whereby the belt is adjustable to have a length that forces the compression member to reside snugly on the victim about the snake bite with the compression member held securely in position.

11. A snake bite treatment device, comprising:
a compression member held in place by a securing member, the securing member configured to cooperate with the compression member, the compression member having a monolithic primary body with upwardly projecting connectors on outer edge portions thereof and with an open center surrounded by a wall that extends downwardly in a direction opposite the securing member connectors that is configured to surround a snake bite and compress skin in a closed perimeter extending about the snake bite a distance inward sufficient to deform the skin inward relative to skin in a center space of the compression member over the snake bite to isolate venom from the bite to thereby impede the venom from entering a victim's lymphatic system,
wherein the securing member comprises a belt that has an adjustable length and two opposing free end portions with a rigid connector on each of the two opposing end portions, and wherein, in position, a user attaches the securing member rigid connectors to the compression member connectors to hold the compression member in position snugly against the victim's body.

12. A first aid snake-bite treatment device, comprising:
a localized compression member having a monolithic primary body with an open medial cavity surrounded by a wall, wherein, in position, the compression member resides on a skin surface of a victim such that the cavity resides over tissue proximate a snake bite and the wall surrounds and compresses localized tissue inward a distance away from and surrounding the snake bite in a closed perimeter to deform the skin inward relative to skin under the cavity of the compression member over the snake bite, wherein the primary body wall extends between upper and lower surfaces of the compression member primary body, and wherein the compression member primary body includes first and second spaced apart belt connection members residing opposite each other across the cavity on respective outer edge portions of the primary body that project outwardly a distance above the upper surface of the primary body; and
a belt having opposing end portions, wherein each end portion is configured to fixedly or releasably attach to the belt connection members of the compression member so that a ring attached to one end of the belt resides proximate the outer surface of the compression member held by the belt connector and extends outwardly from a respective side of the compression member.

13. A snake bite treatment kit, comprising:
at least one belt or other securing member sized and configured to reside about a torso of a person, the belt or other securing member having end portions; and
a compression member configured to attach to the at least one belt or other securing member, wherein the compression member has a primary body having an interior wall that surrounds an open center portion and extends between upper and lower surfaces of the compression member primary body, and wherein the compression member primary body includes first and second spaced apart belt or other securing member connection members residing opposite each other on opposing sides of the open center portion on an outer edge portion of the primary body that project outwardly to extend a distance above the upper surface of the primary body, wherein the belt or other securing member end portions attach to the compression member connection members.

14. The device of claim 13, wherein the belt extends outwardly from a respective side of the compression member.

15. A method of performing first aid treatment of a venomous snake bite, comprising:
placing a localized compression member over a snake bite region on a surface of skin of a victim, wherein the compression member has a primary body having an interior wall that surrounds an open center portion and extends between upper and lower surfaces of the compression member primary body, and wherein the compression member primary body includes first and second spaced apart belt connection members residing opposite each other on opposing sides of the open center portion on an outer edge portion of the primary body that project outwardly a distance above the upper surface of the primary body;
placing a belt around the victim;
tightening the belt and securing the compression member to the victim; and
compressing the skin of the victim surrounding the snake bite using the compression member so that the compressed skin is forced inward a distance relative to the skin proximate the snake bite in a closed perimeter lymphatic compression configuration to impede the venom from entering a victim's lymphatic system.

16. A method according to claim 15, wherein the compressing step is automatically carried out responsive to the tightening step after the placing steps, and wherein the belt has a width that is substantially the same as a largest width dimension of the compression body.

17. The method of claim 15, wherein the placing step is carried out by placing the compression member over a snake bite on a torso of a victim.

18. The method of claim 15, wherein the compression member has a pair of outwardly extending fingers with upper edges that face inward, and wherein the tightening step is carried out by first attaching a rigid belt connector to each of the fingers, then tightening the belt.

19. A method of performing first aid treatment of a venomous snake bite, comprising:
placing a localized compression member over a snake bite region on a surface of skin of a victim, the compression member having a maximum width and a length and a monolithic primary body with upwardly projecting connectors on outer edge portions thereof that extend a distance above the primary body, the primary body having an open center space surrounded by a wall that extends downwardly in a direction opposite the securing member connectors that is configured to surround a snake bite;
securing the compression member to the victim by attaching at least one belt to the connectors so that the at least one belt extends outwardly away from the connectors; and
compressing the skin of the victim surrounding the snake bite using the at least one belt, the belt having a width that is substantially the same as the compression member maximum width so that the compressed skin is forced inward a distance relative to the skin proximate the snake bite thereby impeding snake bite venom from migration into a victim's lymphatic system.

20. The method of claim 19, wherein the placing step is carried out by placing the compression member over a snake bite on a torso of a victim.

21. A snake bite treatment device, comprising:
a compression member held in place by a securing member, the securing member configured to cooperate with the compression member, the compression member having a monolithic primary body with upwardly projecting securing member connectors on outer edge portions thereof that extend a distance above the primary body, the primary body having an open center space surrounded by a wall that extends downwardly in a direction opposite the securing member connectors that is configured to surround a snake bite and compress skin in a closed perimeter extending about the snake bite a distance inward sufficient to deform the skin inward relative to skin in the center space of the compression member over the snake bite to isolate venom from the bite to thereby impede the venom from entering a victim's lymphatic system, wherein the compression member primary body is a substantially oval frame-like body with the open center space defining a large open center with a long dimension of between about 2-5 inches and a largest width dimension of between about 1-3 inches, and wherein, in position, the large open center resides over the snake bite, and wherein the wall is configured to extend substantially orthogonally a distance and a direction that is into a victim's body to force the skin thereunder to compress a suitable distance; and a visually transmissive film or mesh covering residing above and over the open center space of the compression member.

22. The device of claim 11, wherein the belt or other securing member extends outwardly from a respective side of the compression member.

* * * * *

UNITED STATES PATENT AND TRADEMARK OFFICE
CERTIFICATE OF CORRECTION

PATENT NO. : 8,641,731 B2
APPLICATION NO. : 12/347012
DATED : February 4, 2014
INVENTOR(S) : Jason B. Hack It is certified that error appears in the above-identified patent and that said Letters Patent is hereby corrected as shown below:

In the Claims:

Column 7, Claim 1, Line 22: Please correct "opposite the connector, and wherein"
to read -- opposite the connectors, and wherein --

Column 9, Claim 14, Lines 66-67: Please correct "the belt extends outwardly"
to read -- the belt or other securing member extends outwardly --

Column 11, Claim 22: Please replace Claim 22 in its entirety to read as follows:

A first aid snake-bite treatment device, comprising:
a localized compression member having a monolithic primary body with an open medial cavity surrounded by a wall, wherein, in position, the compression member resides on a skin surface of a victim such that the cavity resides over tissue proximate a snake bite and the wall surrounds and compresses localized tissue inward a distance away from and surrounding the snake bite in a closed perimeter to deform the skin inward relative to skin under the cavity of the compression member over the snake bite, wherein the primary body wall extends between upper and lower surfaces of the compression member primary body, and wherein the compression member primary body includes first and second spaced apart belt connection members residing opposite each other across the cavity on respective outer edge portions of the primary body that project outwardly a distance above the upper surface of the primary body;
a belt having opposing end portions, wherein each end portion is configured to fixedly or releasably attach to the belt connection members of the compression member so that a ring attached to one end of the belt resides proximate the outer surface of the compression member held by the belt connector and extends outwardly from a respective side of the compression member; and
a visually transmissive film or mesh covering residing above and over the cavity of the compression member.

Signed and Sealed this
Eleventh Day of November, 2014

Michelle K. Lee
*Deputy Director of the United States Patent and Trademark Office*